(12) United States Patent
Bahal et al.

(10) Patent No.: US 6,235,733 B1
(45) Date of Patent: May 22, 2001

(54) ORAL LIQUID FORMULATIONS OF BENZOXAZINONES HIV REVERSE TRANSCRIPTASE INHIBITORS

(75) Inventors: Surendra M. Bahal, Wayne, PA (US); Michael B. Maurin, Wilmington, DE (US)

(73) Assignee: DuPont Pharmaceuticals Company, Wilmington, DE (US)

( * ) Notice: Subject to any disclaimer, the term of this patent is extended or adjusted under 35 U.S.C. 154(b) by 0 days.

(21) Appl. No.: 09/250,508

(22) Filed: Feb. 16, 1999

Related U.S. Application Data

(60) Provisional application No. 60/074,881, filed on Feb. 17, 1998.

(51) Int. Cl.[7] .................................................. A61K 31/535
(52) U.S. Cl. ......................................... 514/230.5; 544/92
(58) Field of Search ............................ 514/230.5; 544/92

(56) References Cited

U.S. PATENT DOCUMENTS

| | | | |
|---|---|---|---|
| 5,494,936 | * 2/1996 | Sanchez et al. | 514/712 |
| 5,519,021 | 5/1996 | Young et al. | 514/230.5 |
| 5,981,479 | * 11/1999 | Ko et al. | 514/11 |

FOREIGN PATENT DOCUMENTS

| | | |
|---|---|---|
| 9520389 | 8/1995 | (WO) . |
| 9740833 | 11/1997 | (WO) . |

* cited by examiner

*Primary Examiner*—Kathleen K. Fonda
(74) *Attorney, Agent, or Firm*—Norbert F. Reinert; David H. Vance

(57) ABSTRACT

A palatable oral liquid pharmaceutical composition of benzoxazinone compounds useful as HIV reverse transcriptase inhibitors comprising the benzoxazinone active ingredient in a liquid vehicle comprising medium chain fatty acid triglycerides. Other formulating agents such as sweetening agents, lecithin suspending agents, etc. may be optionally added.

20 Claims, No Drawings

ORAL LIQUID FORMULATIONS OF BENZOXAZINONES HIV REVERSE TRANSCRIPTASE INHIBITORS

This application claims the benefit of U.S. Provisional Application No. 60/074,881, filed Feb. 17, 1998.

BACKGROUND OF THE INVENTION

The present invention relates to palatable pharmaceutical compositions of benzoxazinone compounds which are useful in the inhibition of a retrovirus designated human immunodeficiency virus (HIV), the prevention or treatment of infection by HIV and in the treatment of the resulting acquired immune deficiency syndrome (AIDS).

Of particular interest for the present invention is the class of benzoxazinone compounds disclosed in U.S. Pat. No. 5,519,021. Representative of this class of compounds is the compound (−) 6-chloro-4 cyclopropyl-ethynyl-4-trifluoromethyl-1,4 dihydro-2H-3,1-Benzoxazin-2-one.

It has been found that these benzoxazinone compounds in aqueous formulations cause unwanted irritation and burning in the throat on oral administration and for that reason would be unsuitable formulations for marketing. Also, it has been found that traditional non-aqueous solvents such as propylene glycol, alcohol and polyethylene glycols do not significantly improve their palatability. Furthermore, a solution of these drugs in mineral oil was also found unacceptable.

Therefore, it is an object of the present invention to provide oral liquid compositions of benzoxazinone HIV reverse transcriptase inhibitors which are palatable and pleasant when ingested.

SUMMARY OF THE INVENTION

The present invention relates to palatable oral liquid compositions comprising a benzoxazinone HIV reverse transcriptase inhibitor and a liquid vehicle comprising polyol esters of medium chain fatty acids. Other components which may be present in the compositions of the present invention include sweetening agents, emulsifying agents, antimicrobial preservatives, suspending agents, flavoring agents, colorants, antioxidants, or topical oral anesthetics.

In the compositions of the present invention, the benzoxazinone compound is in solution in the medium chain fatty acid ester component but when insoluble sweetening agents are employed the compositions take on the physical appearance of a suspension.

DETAILED DESCRIPTION OF THE INVENTION

A main component of the composition of the present invention is the benzoxazinone inhibitor present in a therapeutically effective amount.

As previously mentioned, compounds of the class disclosed in U.S. Pat. No. 5,519,021 are of particular interest for the compositions of the invention. The disclosure of U.S. Pat. No. 5,519,021 in its entirety is hereby incorporated by reference as a detailed disclosure of the class of benzoxinone inhibitors which is regarded as useful in compositions of the present invention and are intended to be included in the term "benzoxazinone HIV transcriptase inhibitor agent" as used herein. Especially preferred is the compound (−) 6-chloro-4 cyclopropyl-ethynyl-4-trifluoromethyl-1,4 dihydro-2H-3,1-Benzoxazin-2-one, having the generic drug name "efavirenz" However, compounds from other related compound classes found to be active HIV reverse transcriptase inhibitors may be suitable as the active therapeutic agent in the compositions of the present invention, and when such is the case, also are included in the term "benzoxazinone HIV reverse transcriptase inhibitor agent" as used herein.

The concentration of the HIV reverse transcriptase inhibitor agent in the composition will vary depending on the nature of the patient, the therapeutic effect desired, the size of the dosage unit employed, the frequency of dosing and on other considerations well within the knowledge of those with skill in the pharmaceutical arts.

In general, the range for the HIV reverse transcriptase inhibitor agent in the composition can vary from 0.1 to 15% by weight (wgt). More preferably, the drug substance component will range from 1 to 5% by weight in the composition.

The other main component of the composition of this invention is the liquid vehicle composed of polyol esters of medium chain fatty acids. This term "polyol esters of medium chain fatty acids" is intended to include esters and mixed esters of glycerol, propylene glycol or other open chain polyols such as polyethylene glycol, reacted with medium chain fatty acids, wherein said acid has a chain length between 6 and 12 carbon atoms.

Particularly preferred for compositions of the present invention are triglycerides or diglycerides of the $C_8$–$C_{10}$ fatty acids commercially available from the fractionation of coconut oil. Commercially available products of this description are sold under the trade names "Miglyol" and "Captex 300" which are described as having a typical composition of about 68% $C_8$ fatty acid (caprylic) triglyceride and about 28% $C_{10}$ fatty acid (capric) triglyceride with minor levels of $C_6$ and $C_{14}$ fatty acid triglycerides.

The medium chain fatty acid ester component serves as the solvent vehicle for the active agent in formulating the compositions of the invention and is present in the composition in the range from 50 to 99%, by weight more preferably from 70% to 99% by weight.

Preferably, the compositions of the invention will contain a sweetening agent which is useful in reducing the oily taste of the medium chain fatty acid ester and thus contributes in a significant way in making the compositions more palatable.

The sweetening agent can be selected from a sugar such as sucrose, mannitol, sorbitol, xylitol, lactose, etc. or a sugar substitute such as cyclamate, saccaharin, aspartame, etc. If sugar substitutes are selected as the sweetening agent the amount employed in the compositions of the invention will be substantially less than if sugars are employed. Taking this into account, the sweetening agent can be used in the composition in the range of from 0.1 to 50% by weight and more preferably in the range of 0.5 to 30% by weight.

The more preferred sweetening agents are the sugars and particularly sucrose. The particle size of the powdered sucrose used has been found to have a significant influence in the physical appearance of the finished composition and its ultimate acceptance for taste. The preferred particle size of the sucrose component when used is in the range of from 200 to less than 325 mesh US Standard Screen.

The compositions of the present invention can also contain other components routinely utilized in formulating pharmaceutical compositions.

One example of such components is lecithin. Its use in compositions of the invention as an emulsifying agent in the range of from 0.05 to 1% by weight, more preferably from 0.1 to 0.5% by weight may possibly serve to improve absorption of the active drug agent. Other examples of components that may be used are antimicrobial preservatives, such as benzoic acid or parabens; suspending agents, such as colloidal silicon dioxide; antioxidants; topical oral anesthetics; flavoring agents; and colorants.

The selection of such optional components and their level of use in the compositions of the invention is within the level of skill in the art and will be even better appreciated from the working examples provided hereinafter.

In Examples I–IV, lecithin, benzoic acid or parabens preservative, when used, are first-dissolved in the caprylic-capric trigycerides using a Lightnin® mixer or other suitable mixer. The drug is then dissolved in the vehicle. When used, colloidal silicon dioxide is then dispersed and color and flavor are added. Sucrose or other sweetening agent, when used, is then added and the mixture is stirred to obtain a homogeneous dispersion in the vehicle. The order of adding ingredients can be varied to prepare an elegant looking suspension.

The drug is in solution but the product has the appearance of an elegant pharmaceutical suspension. Without being bound by the mechanism of prevention of unwanted throat burning irritation, it appears that the solubilization of the drug in caprylic-capric triglyceride prevents the direct contact of the drug with the oral mucosa while the product is swallowed due to the inability of the drug to partition out of the oil until digestion.

EXAMPLE I

| Formulation Ingredient | Composition, Per 100 mL | |
|---|---|---|
| | I | II |
| Efavirenz Drug Substance | 0.1 g | 15 g |
| Caprylic-Capric Acid Triglycerides qs ad | 100 mL | 100 mL |

EXAMPLE II

| Formulation Ingredient | Composition, Per 100 mL |
|---|---|
| Efavirenz Drug Substance | 2 g |
| Colloidal Silicon Dioxide, NF | 0.1 g |
| Ferric Oxide, NF (colorant) | 0.1 g |
| Strawberry Flavor | 0.04 g |
| Confectioner's Sugar, NF | 30 g |
| Caprylic-Capric Acid Triglycerides, qs ad | 100 mL |

EXAMPLE III

| Formulation Ingredient | Composition, Per 100 mL |
|---|---|
| Efavirenz Drug Substance | 2 g |
| Lecithin, NF | 0.5 g |
| Benzoic Acid, USF | 0.1 g |
| Colloidal Silicon Dioxide, NF | 1.5 g |
| Ferric Oxide, NF (colorant) | 0.1 g |
| Strawberry Flavor | 0.04 g |
| Confectioner's Sugar, NF | 30 g |
| Capyrlic-Capric Acid Triglycerides, qs ad | 100 mL |

EXAMPLE IV

| Formulation Ingredient | Composition, Per 100 ml | | | | |
|---|---|---|---|---|---|
| | A | B | C | D | E |
| Efavirenz Drug Substance | 0.1 g | 10 g | 2 g | 5 g | 0.1 g |
| Lecithin, NF | 0.05 g | — | — | 0.1 g | 0.5 g |
| Benzoic Acid, USF | 0.1 g | 0.1 g | 0.2 g | — | — |
| Methyl-paraben, NF | — | 0.1 g | — | — | 0.1 g |
| Propyl-paraben, NF | — | 0.02 g | — | 0.1 g | 0.02 g |
| Colloidal Silicon Dioxide, NF | 0.2 g | 0.5 g | 0.1 g | 0.2 g | — |
| Colorant | — | qs | — | qs | — |
| Flavor | — | qs | qs | — | — |
| Sucrose, NF, Fine Powder | 10 g | 50 g | — | — | — |
| Mannitol, USP, Fine Powder | — | — | 30 g | — | 30 g |
| Sorbitol, NF, Fine Powder | — | — | — | 30 g | — |
| Caprylic-Capric Acid Triclycerides, Ph. Eur. qs ad | 100 mL | 100 mL | 100 mL | 100 mL | 100 mL |

Each of the above formulations from Examples I–IV can be administered orally by from less than 1 to several teaspoons per day to a patient in need of treatment for AIDS.

In another embodiment of the invention, the liquid formulation of the invention can be encapsulated in a soft gelatin capsule for oral administrtion to patients. This is illustrated by the following working example:

EXAMPLE V

| Efavirenz Drug Substance | 20 g |
|---|---|
| Capyrlic-Capric Acid Triglycerides | 130 g |

The above quantities of drug substance and triglycerides were mixed together in a suitable vessel until the drug substance was fully dissolved in the triglycerides.

The resulting solution was then filled in soft gelatin capsules of a conventional type utilizing conventional pharmaceutical manufacturing equipment for their purpose. Soft gelatin capsules, in addition to containing gelatin and water usually contain a plasticizer such as glycerin and/or sorbital. Additional ingredients, such as coloring and opacifying agents may also be included.

If desired, the filling prepared as described above also may be encapsulated in hard gelatin capsule shells.

What is claimed is:

1. A liquid pharmaceutical composition for oral administration comprising from 1 to 5% by weight of a benzoxazinone HIV reverse transcriptase inhibitor agent and from 50 to 99% by weight of a liquid vehicle comprising polyol esters of medium chain fatty acids.

2. The composition of claim 1 wherein the benzoxazinone HIV reverse transcriptase inhibitor agent is (−)6-chloro-4 cyclopropyl-ethynyl-4-trifluoromethyl-1,4 dihydro-2H-3,1-Benzoxazin-2-one.

3. The composition of claim 1, wherein the polyol esters of medium chain fatty acids consist essentially of $C_8$ and $C_{10}$ fatty acid triglycerides.

4. The composition of claim 1 contained in a soft gelatin capsule.

5. The composition of claim 1, which contains a sweetening agent in a range of from 0.1 to 50% by weight.

6. The composition of claim 5 wherein the sweetening agent is sucrose.

7. A liquid pharmaceutical composition for oral administration containing from 1 to 5% by weight of a benzoxazinone HIV reverse transcriptase inhibitor agent, from 70 to 99% by weight $C_8$–$C_{10}$ fatty acid triglycerides, from 0.5 to 30% by weight of a sweetening agent and from 0.1 to 0.5% by weight lecithin.

8. The composition of claim 7 wherein the benzoxazinone HIV reverse transciptase inhibitor agent is (−)6-chloro-4 cyclopropyl-ethynyl-4-trifluoromethyl-1,4 dihydro-2H-3,1-Benzoxazin-2-one.

9. The composition of claim 7 wherein the sweetening agent is sucrose having a particle size of from 200 to less than 325 mesh US Standard Screen.

10. The composition of claim 1, further comprising 0.05 to 1% by weight of lecithin.

11. The composition of claim 10, wherein the composition comprises 0.1 to 0.5% by weight of lecithin.

12. The composition of claim 1, wherein the composition comprises from 70 to 99% by weight of the liquid vehicle.

13. The composition of claim 1, wherein the polyol esters of medium chain fatty acids consist essentially of $C_8$–$C_{10}$ fatty acid triglycerides.

14. The composition of claim 1, wherein the polyol esters of medium chain fatty acids consist essentially of 68% of caprylic triglyceride and 28% of capric triglyceride.

15. The composition of claim 5, wherein the composition comprises from 0.5 to 30% by weight of a sweetening agent and the sweetening agent is sucrose having a particle size of from 200 to less than 325 mesh US Standard Screen.

16. A liquid pharmaceutical composition for oral administration comprising from 1–5% by weight of a benzoxazinone HIV reverse transcriptase inhibitor agent and from 50–99% by weight of $C_8$–$C_{10}$ fatty acid triglycerides.

17. The composition of claim 16, wherein the agent is (−)6-chloro-4-cyclopropyl-ethynyl-4-trifluoromethyl-1,4-dihydro-2H-3,1-benzoxazin-2-one and the composition comprises from 70–99% by weight of the fatty acid triglycerides and the fatty acid triglycerides consist essentially of 68% of caprylic triglyceride and 28% of capric triglyceride.

18. The composition of claim 17, further comprising from 0.1–50% by weight of a sweetening agent and from 0.05–1% by weight of lecithin.

19. The composition of claim 18, wherein the composition comprises from 0.5–30% of a sweetening agent and from 0.1–0.5% by weight of lecithin, wherein the sweetening agent is sucrose.

20. The composition of claim 19, wherein the sucrose has a particle size of from 200 to less than 325 mesh US Standard Screen and the composition is encapsulated in a soft gelatin capsule.

\* \* \* \* \*